US008652031B2

(12) United States Patent
Kirschenman

(10) Patent No.: US 8,652,031 B2
(45) Date of Patent: Feb. 18, 2014

(54) REMOTE GUIDANCE SYSTEM FOR MEDICAL DEVICES FOR USE IN ENVIRONMENTS HAVING ELECTROMAGNETIC INTERFERENCE

(75) Inventor: Mark B. Kirschenman, Waverly, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 11 days.

(21) Appl. No.: 13/339,683

(22) Filed: Dec. 29, 2011

(65) Prior Publication Data

US 2013/0172812 A1     Jul. 4, 2013

(51) Int. Cl.
*A61B 1/00*     (2006.01)

(52) U.S. Cl.
USPC ........................... 600/152; 600/146; 604/528

(58) Field of Classification Search
USPC .................................. 604/528; 600/146, 152
See application file for complete search history.

(56) References Cited

U.S. PATENT DOCUMENTS

| | | | |
|---|---|---|---|
| 4,991,957 A | 2/1991 | Sakamoto et al. | |
| 5,993,463 A * | 11/1999 | Truwit | 606/130 |
| 6,507,751 B2 | 1/2003 | Blume et al. | |
| 6,603,993 B1 | 8/2003 | Coutts et al. | |
| 6,790,175 B1 | 9/2004 | Furusawa et al. | |
| 6,846,286 B2 * | 1/2005 | Suzuki et al. | 600/145 |
| 6,860,878 B2 | 3/2005 | Brock et al. | |
| 7,090,683 B2 | 8/2006 | Brock et al. | |
| 7,104,953 B2 * | 9/2006 | Hirata et al. | 600/152 |
| 7,169,141 B2 | 1/2007 | Brock et al. | |
| 7,214,230 B2 | 5/2007 | Brock et al. | |
| 7,297,142 B2 | 11/2007 | Brock | |
| 7,371,210 B2 | 5/2008 | Brock et al. | |
| 7,699,835 B2 | 4/2010 | Lee et al. | |
| 7,789,874 B2 | 9/2010 | Yu et al. | |
| 7,850,642 B2 | 12/2010 | Moll et al. | |
| 7,922,693 B2 * | 4/2011 | Reis | 604/119 |
| 7,963,288 B2 | 6/2011 | Rosenberg et al. | |
| 7,972,298 B2 | 7/2011 | Wallace et al. | |
| 7,974,681 B2 | 7/2011 | Wallace et al. | |
| 8,005,537 B2 | 8/2011 | Hlavka et al. | |
| 8,021,326 B2 | 9/2011 | Moll et al. | |
| 8,052,621 B2 | 11/2011 | Wallace et al. | |
| 8,052,636 B2 | 11/2011 | Moll et al. | |

(Continued)

OTHER PUBLICATIONS

International Search Report issued in corresponding international application PCT/US2012/022880 (May 23, 2012).

(Continued)

*Primary Examiner* — Laura Bouchelle
(74) *Attorney, Agent, or Firm* — Dykema Gossett PLLC

(57) ABSTRACT

A remote guidance system for a medical device is provided that is capable of use with magnetic resonance imaging and other environments with a relatively high level of electromagnetic interference. In one embodiment, a fluid control system controls delivery of fluid to a fluid conduit supplying a fluid chamber of a fluid housing. A piston disposed within the fluid chamber moves in response to a change in fluid displacement in the chamber and causes corresponding movement of the medical device within a body. In another embodiment, means are provided for controlling a connector coupled to the medical device at a location outside the body wherein movement of the connector causes a corresponding movement of the medical device. A sensor generates a signal indicative of a characteristic associated with movement of the medical device. The sensor includes an optic fiber that transmits a light wave indicative of the characteristic.

26 Claims, 17 Drawing Sheets

(56) References Cited

U.S. PATENT DOCUMENTS

| | | | |
|---|---|---|---|
| 8,092,397 B2 | 1/2012 | Wallace et al. |
| 8,108,069 B2 | 1/2012 | Stahler et al. |
| 8,146,874 B2 | 4/2012 | Yu |
| 8,190,238 B2 | 5/2012 | Moll et al. |
| 2001/0031983 A1 | 10/2001 | Brock et al. |
| 2003/0135204 A1 | 7/2003 | Lee et al. |
| 2004/0049205 A1 | 3/2004 | Lee et al. |
| 2004/0176751 A1 | 9/2004 | Weitzner et al. |
| 2006/0089535 A1* | 4/2006 | Raz et al. ............... 600/152 |
| 2006/0200026 A1 | 9/2006 | Wallace et al. |
| 2007/0016006 A1 | 1/2007 | Shachar |
| 2007/0088340 A1 | 4/2007 | Brock et al. |
| 2007/0106317 A1 | 5/2007 | Shelton et al. |
| 2007/0197896 A1 | 8/2007 | Moll et al. |
| 2007/0238927 A1 | 10/2007 | Ueno et al. |
| 2008/0027464 A1 | 1/2008 | Moll et al. |
| 2008/0058836 A1 | 3/2008 | Moll et al. |
| 2008/0082109 A1 | 4/2008 | Moll et al. |
| 2008/0140087 A1 | 6/2008 | Barbagli et al. |
| 2008/0195081 A1 | 8/2008 | Moll et al. |
| 2008/0243064 A1 | 10/2008 | Stahler et al. |
| 2008/0249536 A1 | 10/2008 | Stahler et al. |
| 2008/0255505 A1 | 10/2008 | Carlson et al. |
| 2008/0262513 A1 | 10/2008 | Stahler et al. |
| 2008/0300592 A1 | 12/2008 | Weitzner et al. |
| 2009/0012533 A1 | 1/2009 | Barbagli et al. |
| 2009/0024141 A1 | 1/2009 | Stahler et al. |
| 2009/0036900 A1 | 2/2009 | Moll et al. |
| 2009/0105639 A1 | 4/2009 | Weitzner et al. |
| 2009/0138025 A1 | 5/2009 | Stahler et al. |
| 2009/0157092 A1 | 6/2009 | Blumenkranz et al. |
| 2009/0247943 A1 | 10/2009 | Kirschenman et al. |
| 2010/0170519 A1 | 7/2010 | Romo et al. |
| 2010/0175701 A1 | 7/2010 | Reis et al. |
| 2010/0256558 A1 | 10/2010 | Olson et al. |
| 2010/0331856 A1 | 12/2010 | Carlson et al. |
| 2011/0015648 A1 | 1/2011 | Alvarez et al. |
| 2011/0295247 A1 | 12/2011 | Schlesinger et al. |
| 2011/0295248 A1 | 12/2011 | Wallace et al. |
| 2011/0295267 A1 | 12/2011 | Tanner et al. |
| 2011/0295268 A1 | 12/2011 | Roelle et al. |
| 2011/0319714 A1 | 12/2011 | Roelle et al. |
| 2011/0319815 A1 | 12/2011 | Roelle et al. |
| 2011/0319910 A1 | 12/2011 | Roelle et al. |
| 2012/0191086 A1 | 7/2012 | Moll et al. |

OTHER PUBLICATIONS

Written Opinion issued in corresponding international application PCT/US2012/022880 (May 23, 2012).

* cited by examiner

REMOTE GUIDANCE SYSTEM FOR MEDICAL DEVICES FOR USE IN ENVIRONMENTS HAVING ELECTROMAGNETIC INTERFERENCE

BACKGROUND OF THE INVENTION a. Field of the Invention

This invention relates to remote guidance systems for medical devices within a body. In particular, the instant invention relates to remote guidance systems configured for use in environments utilizing magnetic resonance imaging equipment and in other environments having a relatively high degree of electromagnetic interference.

b. Background Art

A wide variety of medical devices are inserted into the body to diagnose and treat a various medical conditions. Catheters, for example, are used for to perform a variety of tasks within human bodies and other bodies including the delivery of medicine and fluids, the removal of bodily fluids and the transport of surgical tools and instruments. In the diagnosis and treatment of atrial fibrillation, for example, catheters may be used to deliver electrodes to the heart for electrophysiological mapping of the surface of the heart and to deliver ablative energy to the surface among other tasks. Catheters are typically routed to a region of interest through the body's vascular system. In a conventional approach, an introducer is inserted through the skin surface and another introducer or sheath having an inner diameter greater than the outer diameter of the catheter is threaded through the vasculature to a region of interest. The catheter is then moved longitudinally through the sheath to the region of interest.

The introducer sheath and catheter, along with other medical devices, are typically maneuvered through the body manually by the physician while visualizing the location of the device relative to the patient's anatomy using an imaging system, such as a fluoroscopic imaging system, or a position, navigation and visualization system that determines the position of the device within the body and generates a representation of the device against an image or model of the patient's anatomy. Manual movement of medical devices within the body requires precise control and is dependent on the skill of the physician. In order to reduce or eliminate potential variability in the procedure due to physician skill and to allow performance of procedures from remote locations, remote guidance systems for medical devices have been developed using electromechanical drive systems to control movement of the devices. Several embodiments of remote control guidance systems are disclosed and illustrated in U.S. Published Patent Application No. 2010-0256558 titled "Robotic Catheter System," U.S. Pat. No. 6,507,751 titled "Method and Apparatus Using Shaped Field of Repositionable Magnet to Guide Implant," and U.S. Published Patent Application No. 2007-0016006 titled "Apparatus and Method for Shaped Magnetic Field Control for Catheter, Guidance, Control, and Imaging," the entire disclosures of which are incorporated herein by reference.

Because conventional remote guidance systems rely on electromechanical drive systems to control movement of the medical device, such systems are not well suited to use in environments where there is a relatively high level of electromagnetic interference from other systems such as in a magnetic resonance imaging environment. As a result, remote guidance systems have not proven useful in such environments despite the benefits provided such systems in terms of control and ease of use.

The inventor herein has recognized a need for a remote guidance system for a medical device within a body that will minimize and/or eliminate one or more of the above-identified deficiencies.

BRIEF SUMMARY OF THE INVENTION

It is desirable to provide a remote guidance system for a medical device in a body. In particular, it is desirable to provide a system that is usable in environments having a relatively high level of electromagnetic interference.

A remote guidance system for navigating a medical device within a body in accordance with one embodiment of the present teachings includes a fluid control system configured to control delivery of fluid to a fluid conduit. The system further includes a fluid actuator including a fluid housing defining a fluid chamber and configured to receive fluid from the fluid conduit and a piston disposed within the fluid chamber and movable within the fluid chamber responsive to a change in fluid displacement within the fluid chamber. The fluid actuator is configured such that movement of the piston causes a corresponding first movement of the medical device within the body.

A remote guidance system for guiding a medical device within a body in accordance with another embodiment of the present teachings includes a connector configured for coupling to the medical device at a location outside of the body. In one embodiment, the connector is coupled to a steering wire of the medical device. The connector is further configured such that movement of the connector causes a corresponding movement of the medical device. The system further includes means for controlling movement of the connector and a sensor generating a signal indicative of a characteristic associated with movement of the medical device. The sensor includes an optic fiber configured to transmit a detected light wave indicative of said first characteristic.

A remote guidance system for steering a medical device within a body in accordance with another embodiment of the present teachings includes a fluid control system configured to control delivery of fluid to a fluid conduit and a manipulator assembly operably coupled to the fluid conduit. The manipulator assembly includes a first connector configured to couple with a steering component of the medical device and a second connector configured to releasably hold the medical device to a fluid actuator at a location outside the body. The manipulator assembly is configured such that when fluid is delivered to the manipulator assembly from the fluid control system, the first connector moves relative to the second connector and such movement causes the medical device to move within the body. The remote guidance system further includes an electronic control unit configured to control said fluid control system.

Remote guidance systems in accordance with the present teachings are advantageous relative to conventional remote guidance systems because the use of fluid based controls and optic sensors enable use of the remote guidance system in environments that are subject to relatively high electromagnetic interference such as magnetic resonance imaging. As a result, the benefits of remote guidance systems, including precise control of the medical device within the body, can be obtained in such environments.

The foregoing and other aspects, features, details, utilities and advantages of the present invention will be apparent from reading the following description and claims, and from reviewing the accompanying drawings.

DETAILED DESCRIPTION OF EMBODIMENTS OF THE INVENTION

Figure 1:
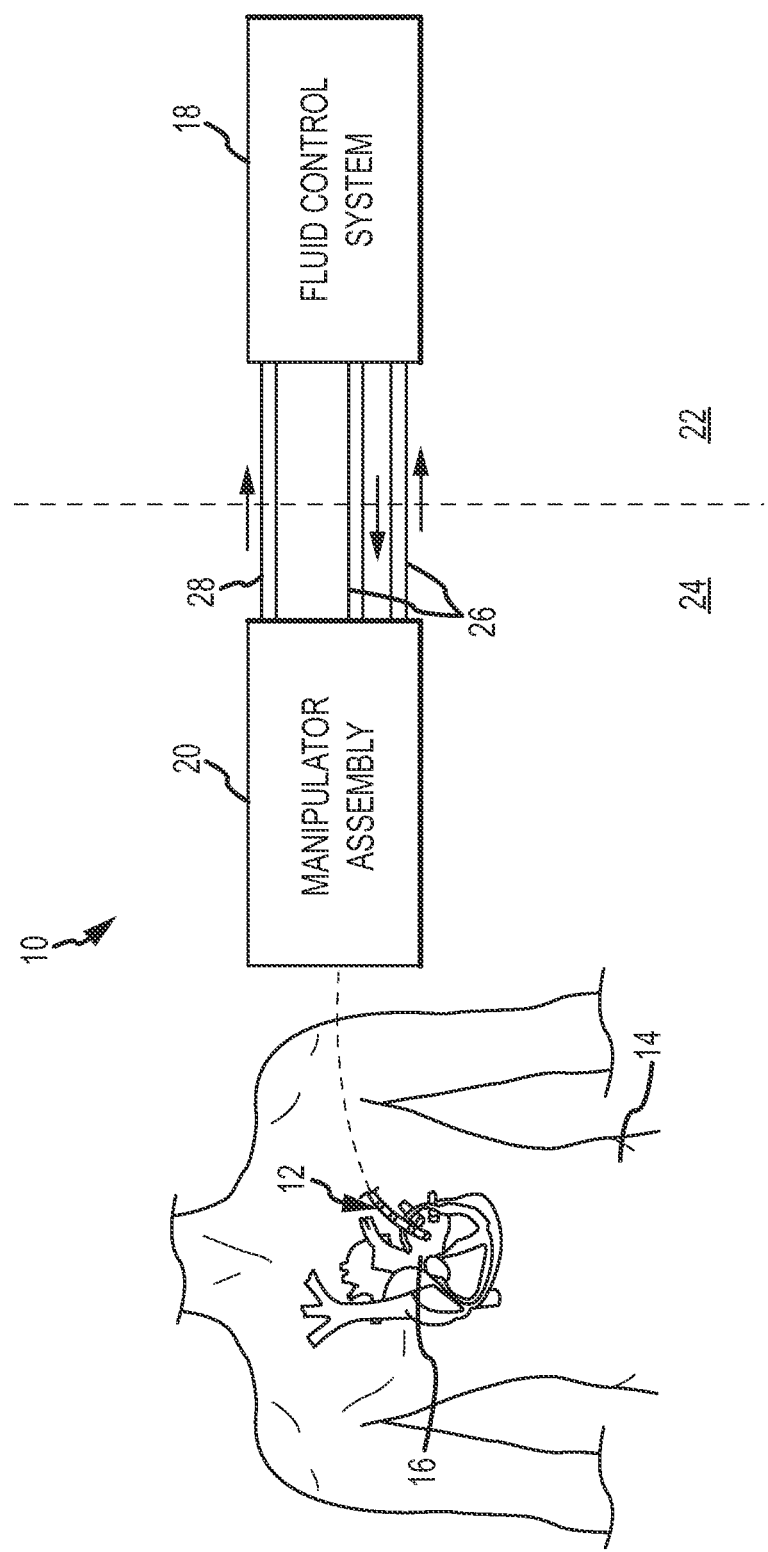
FIG. 1 is a diagrammatic view of remote guidance system for a medical device in accordance with the present teachings.

Referring now to the drawings wherein like reference numerals are used to identify identical components in the various views, FIG. 1 illustrates a remote guidance system 10 for navigating a medical device 12 within a body 14. In the illustrated embodiment, device 12 comprises a catheter for use in diagnosis or treatment of cardiac tissue 16 within body 14. System 10 includes a fluid control system 18 and a manipulator assembly 20 for controlling movement of device 12. As discussed in greater detail hereinbelow, fluid control system 18 and manipulator assembly 20 are relatively remote from one another within an electrophysiology (EP) lab. Fluid control system 18 may be located in a control environment 22 or room which is commonly outfitted with one or more control stations operated by the physician and/or one or more control technicians. Manipulator assembly 20 may be located in a procedure or operating environment 24 or room (i.e. a sterile environment). Depending on the lab setup, the control environment 22 may be across the room from the operating environment 24 or the control and operating environments 22, 24 may be in separate rooms, perhaps configured with a common window to allow the physician and/or technicians to observe the operating environment 24 through the window from the control environment 22. In accordance with various embodiments of the system 10 described and claimed herein, fluid control system 18 and manipulator assembly 20 are coupled by a series of fluid conduits 26 and optic fibers 28. The reduction or elimination of electrical wires and cables between control system 18 and manipulator assembly 20 enables use of system 10 in environments having relatively high levels of electromagnetic interference such as an environment in which the operating environment 24 includes a magnetic resonance imaging system.

As referenced above, device 12 may comprise a deformable catheter of the type used to allow removal of bodily fluids or injection of fluids and medicine into body 14 and/or for transporting surgical tools or instruments within body 14 including those use for pacing or tissue ablation of tissue 16. The catheter may be inserted within a vessel located near the surface of a body (e.g., in an artery or vein in the leg, neck, or arm) in a conventional manner and maneuvered to a region of interest in body 14 such as the heart under the guidance of an imaging system or a position, navigation and visualization system such as the system available commercially under one or more of the trademarks "ENSITE", "ENSITE VELOCITY", and/or "ENSITE NAVX" from St. Jude Medical, Inc. Device 12 may, for example, comprise an electrophysiology (EP) mapping catheter for use in gathering EP data associated with the heart to enable generation of an image of the geometry of the heart surface and related EP data. Device 12 may alternatively comprise an intracardiac echocardiography (ICE) catheter used to generate an image of a region of interest within body 14 such as the heart. Device 12 may alternatively comprise an ablation catheter used to ablate tissue within the heart to treat abnormal heart rhythms such as atrial fibrillation, ventricular tachycardia and similar conditions. Although examples of specific medical devices 12 associated with diagnosis and treatment of conditions associated with the heart have been described, it should be understood that the inventive system 10 may find application in connection with navigating a variety of medical devices in varying locations within human and non-human bodies including, for example, introducer sheaths for use in guiding devices such as catheters to a target region while protecting vessel walls, transseptal needles and endoscopic devices including those used for placements of leads for cardiac rhythm management devices and other medical devices.

Figure 2:
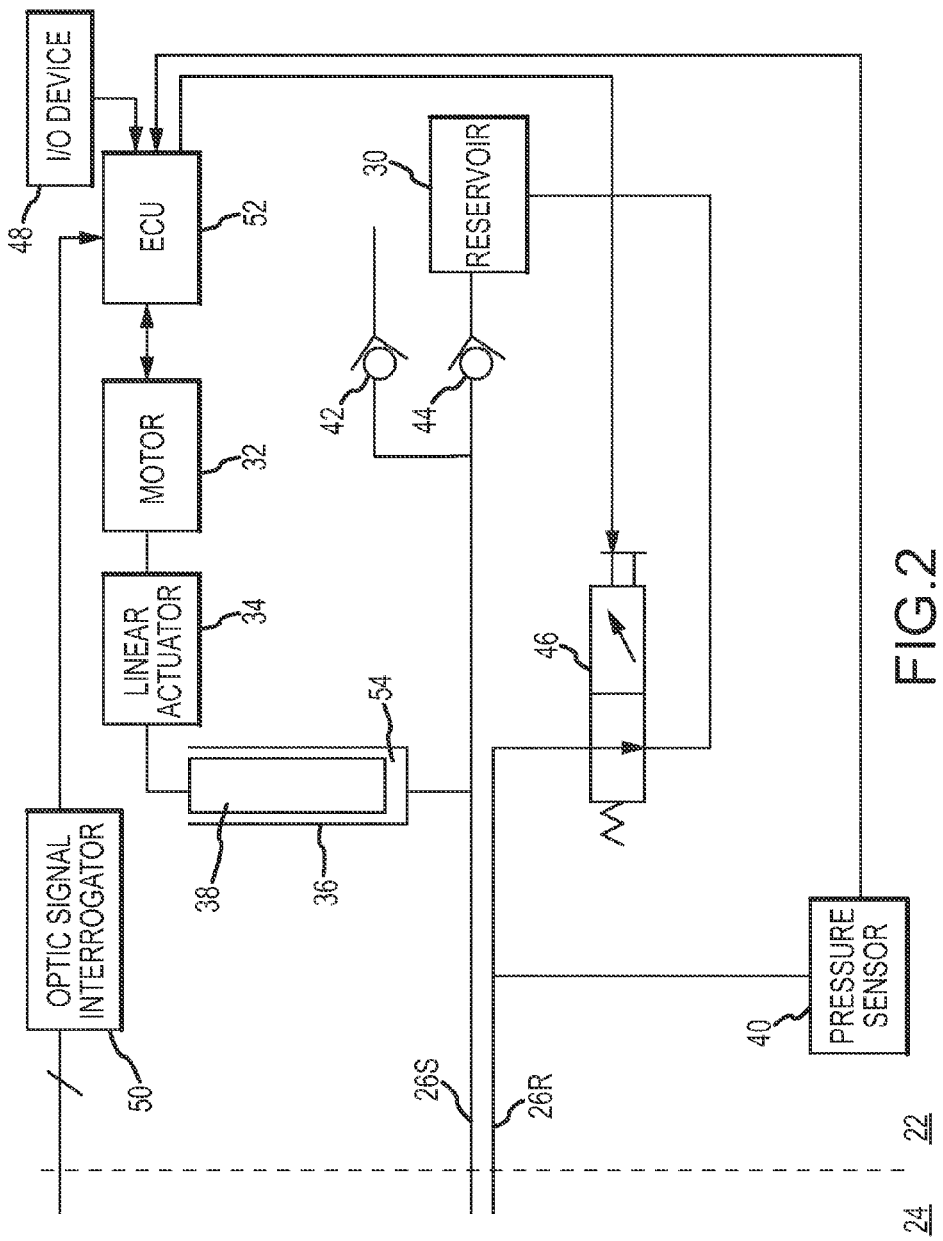
FIG. 2 is a diagrammatic view of one embodiment of a fluid control system for use in the remote guidance system of FIG. 1.

Fluid control system 18 is provided to control the delivery of fluid to manipulator assembly 20. System 18 supplies fluid to assembly 20 and receives fluid from assembly 20 through fluid conduits 26 connecting system 18 and assembly 20. System 18 also receives feedback signals in the form of light waves through optic fibers 28 from sensors on assembly 20 as discussed in greater detail hereinbelow. The components of system 18 may be all located in control environment 22 with only fluid conduits 26 and optic fibers 28 extending between control and operating environments 22, 24 in order to couple system 18 to manipulator assembly 20. Referring to FIG. 2, in one embodiment of the invention, system 18 may include a fluid reservoir 30, a motor 32, a linear actuator 34, a fluid housing 36, a piston 38, a fluid pressure sensor 40, purge valves 42, 44, a release valve 46, an input/output device 48, a signal interrogator 50, and an electronic control unit 52. The embodiment illustrated in FIG. 2 is configured to control a single movement of device 12 such as translation of device 12 within body 14 or deflection of device 12 in one direction within body 14. It should be understood from the description hereinbelow, however, that various elements of the illustrated system 18 can be replicated to enable multiple controlled movements of device 12 or multiple devices 12. In one embodiment, for example, components such as motor 32, actuator 34, fluid housing 36, and piston 38 may be replicated to permit independent translation of both a sheath and a catheter and to permit independent control of four separate steering wires in each of the sheath and the catheter.

Fluid reservoir 30 provides a source of fluid for system 10 and a place for storage of fluid. Reservoir 30 may be made from conventional materials based upon the type of fluid used within system 10. The fluid used within system 10 may be a biocompatible liquid such as saline or other water based liquids or glycerin. It should be understood, however, that pneumatic fluid (i.e. air) could alternatively be used in certain embodiments of the invention. Reservoir 30 is coupled in a conventional manner to supply and return fluid conduits 26S, 26R.

Motor 32 is provided to control movement of piston 38 within fluid housing 36 either directly or indirectly through linear actuator 34. Motor 32 may comprise a conventional electric motor or may comprise a stepper motor. In one embodiment of the invention, motor 32 may comprise a linear motor that outputs a linear force directly to piston 38 (in which case linear actuator 34 may be eliminated). In another embodiment, motor 32 outputs a rotational force or torque that is converted into a linear force by actuator 34 that is then applied to piston 38.

Linear actuator 34 is provided to control movement of piston 38 within fluid housing 36. Actuator 34 may comprise a conventional ball screw actuator in which a plurality of balls are disposed within a thread formed in a screw and movement of the balls in response to torque provided by motor 32 causes linear movement of the screw. It should be understood, however, that actuator could assume a variety of conventional forms including those that output a linear force in response to an input of a rotational force or torque and those that output a linear force in response to an input of a linear force.

Fluid housing 36 defines a fluid chamber 54 that stores a variable amount of fluid in response to movement of piston 38. Fluid housing 36 is made from conventional materials based on the type of fluid used within system 10. Fluid housing 36 defines an output port at one end connected to supply fluid conduit 26S and an opening at an opposite end into which piston 38 extends. Fluid housing 36 is cylindrical in the illustrated embodiment, but it should be understood that the shape of housing may vary.

Piston 38 is provided to control the amount of fluid delivered from fluid chamber 54 to supply fluid conduit 26S. Piston 38 is conventional in the art and may be made from conventional materials based on the type of fluid used within system 10. Piston 38 is coupled to motor 32 directly or indirectly by, for example, actuator 34. Piston 38 is disposed within fluid chamber 54 of fluid housing 36 and is movable within fluid chamber 54 to control the amount of fluid in fluid chamber 54 that is delivered to supply fluid conduit 26S.

Fluid pressure sensor 40 is provided to monitor fluid pressure in manipulator assembly 20. In accordance with one aspect of the present teachings, sensor 40 senses fluid pressure in return fluid conduit 26R. As a result, pressure sensor 40 measures fluid pressure independent of fluid flow pressure drop that occurs in supply fluid conduit 26S due to friction and other factors. Although a single pressure sensor 40 is shown in FIG. 2, it should again be understood that multiple pressure sensors 40 may be employed on corresponding return fluid conduits 26R where system 10 is configured to control multiple movements of device 12 and/or multiple devices 12.

Purge valves 42, 44, are provided to enable air and fluid to be purged from fluid control system 18. In particular, valve 42 is provided to allow fluid to be removed from system 18 for repair, replacement and/or disassembly of system 18. Valve 42 may be disposed in a branch conduit intersecting supply fluid conduit 26S. Valve 44 is provided to allow removal of air from system 18 and introduction of fluid. Valve 44 may be disposed in supply fluid conduit 26S. Valves 42, 44 may further prevent fluid from passing to reservoir 30 during normal operation of system 18. The use of valves 42, 44, in combination with the other components of system 10, enables transportation and delivery of system components without fluid stored therein thereby eliminating risks relating to freezing or leakage of fluids. Further, fluid can be introduced and removed from system 10 upon each use of system 10 or periodically for maintenance or movement of system 10. Valves 42, 44 may comprise conventional check valves.

Release valve 46 is provided to release fluid pressure on system 10 and relax system 10 gently in the event of a power loss of system failure. Valve 46 may comprise a conventional solenoid valve that is energized (closed) during normal operation such that fluid pressure imparted by piston 38 is transmitted to manipulator assembly 20. In the event of a power loss or system failure, valve 46 is deenergized (opened) and returns fluid to reservoir 30 to release pressure on assembly 20.

Input/output (I/O) device 48 is provided to allow a physician to control manipulator assembly 20 to control movement of device 12. Device 48 may include, for example, instrumented traditional catheter handle controls, oversized catheter models, instrumented user-wearable gloves, touch screen display monitors, 2-D input devices, 3-D input devices, spatially detected styluses, and traditional joysticks. These devices may be configured to directly control the movement of device 12, or may be configured, for example, to manipulate a target or cursor on a rendered computer model of the patient's anatomy on a display whose movements are translated by ECU 52 to commands for movement of device 12.

Signal interrogator 50 is provided to convert light waves received from optic fibers 28 into electric signals for use by ECU 52. Interrogator 50 may be similar to other signal interrogators conventional in the art and may be located in control environment 22.

Electronic control unit (ECU) 52 translates motions of the physicians at I/O device 48 into commands used to control motor 32 and, therefore, delivery of fluid to manipulator assembly 20. ECU 52 may be specific to fluid control system 18 or may be used in the control of other conventional systems in an EP lab including, for example, medical device position, navigation and/or visualization systems, imaging systems, EP monitoring systems and other systems. ECU 52 may comprise a programmable microprocessor or microcontroller or may comprise an application specific integrated circuit (ASIC). ECU 52 may include a central processing unit (CPU) and an input/output (I/O) interface through which ECU 52 may receive a plurality of input signals including signals from motor 32, pressure sensor 40, input/output device 48, and signal interrogator 50 and generate a plurality of output signals including those used to control motor 32 and release valve 46.

Figure 3:
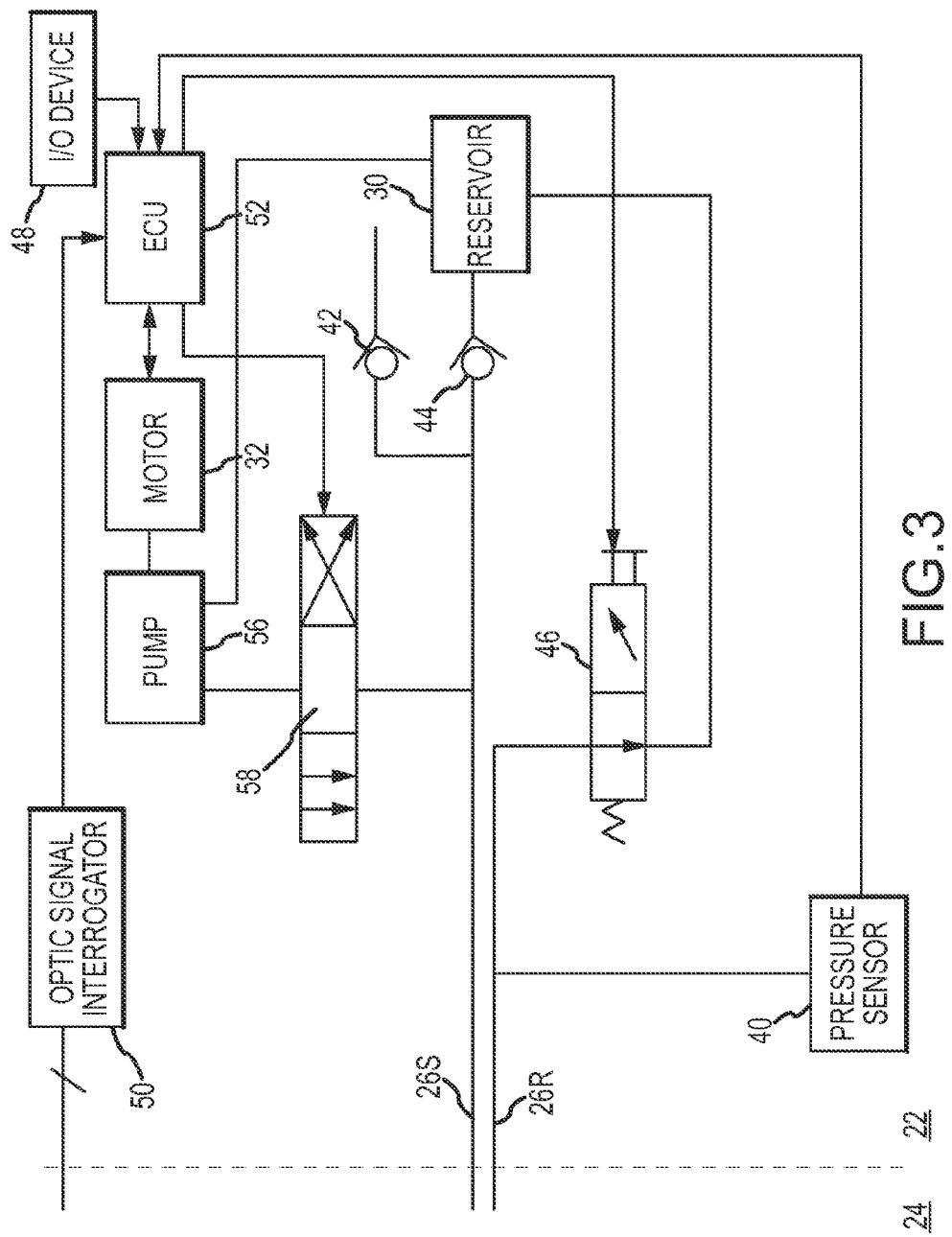
FIG. 3 is a diagrammatic view of another embodiment of a fluid control system for use in the remote guidance system of FIG. 1.

Referring now to FIG. 3, in another embodiment of the invention, system 18 may again include fluid reservoir 30, motor 32, fluid pressure sensor 40, release valve 46, input/output device 48, signal interrogator 50 and ECU 52. In the illustrated embodiment, however, system 18 includes a pump 56 and a valve 58 to provide and control fluid delivery to supply fluid conduit 26S rather than the fluid housing 36 and piston 38 shown in the embodiment in FIG. 2.

Pump 56 is provided to draw fluid from reservoir 30 and direct fluid to fluid supply conduit 26S. Pump 56 may be driven by motor 32 under the control of ECU 52. Pump 56 may provide fluid to multiple supply fluid conduits 26S for use in effecting multiple controlled movements of device 12 or multiple devices 12 including, in one embodiment, independent translation of both a sheath and a catheter and independent control of four separate steering wires in each of the sheath and the catheter.

Valve 58 is configured to control fluid flow in supply fluid conduit 26S by controlling the amount of fluid delivered to supply fluid conduit 26S and, therefore, the fluid supplied to manipulator assembly 20 in order to achieve a predetermined position in assembly 20. Valve 58 may comprise an electro hydraulic servo valve operating under the control of ECU 52. Separate valves 58 may be used to control the delivery of fluid to each supply fluid conduit 26S providing fluid to manipulator assembly 20.

Figure 4:
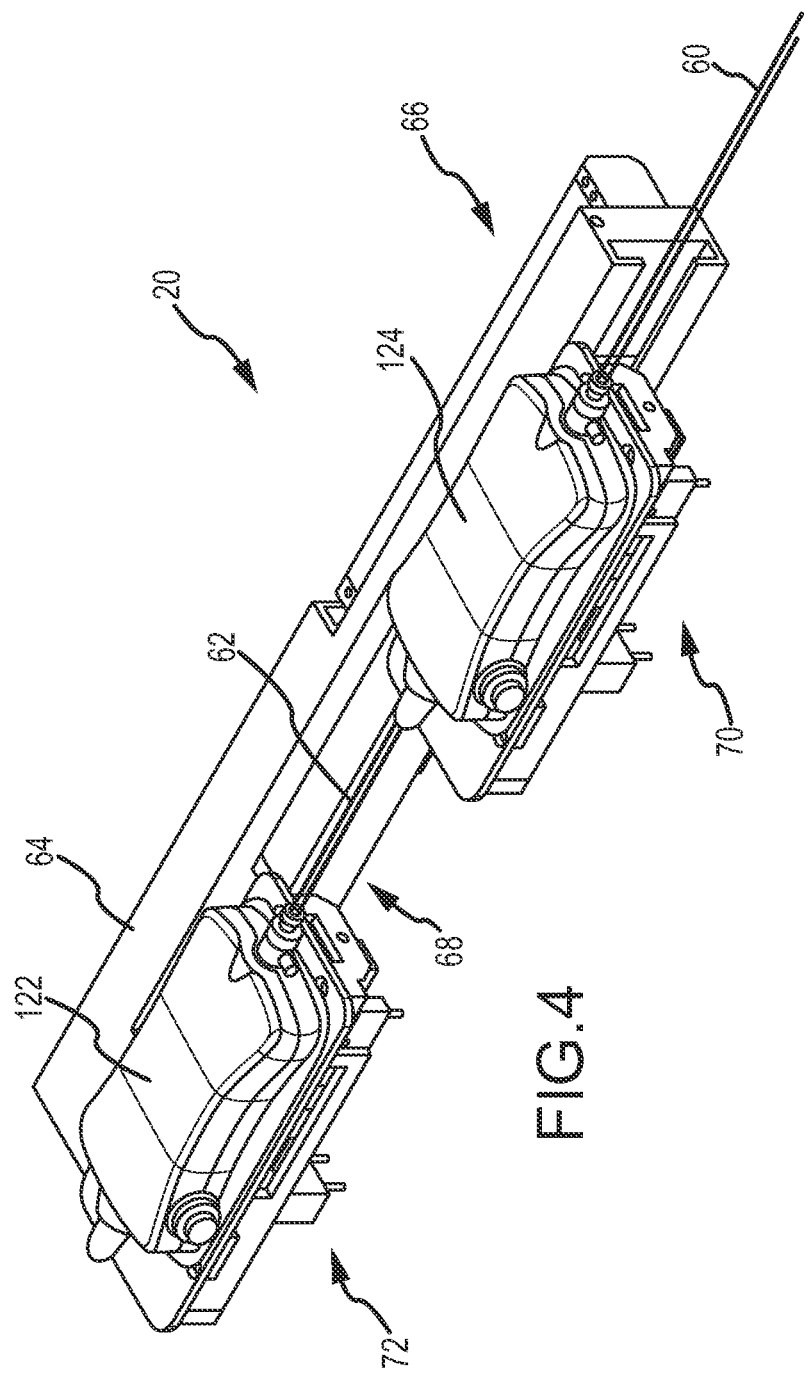
FIGS. 4-5 are perspective view of one embodiment of a manipulator assembly for use in the remote guidance system of FIG. 1.
Figure 5:
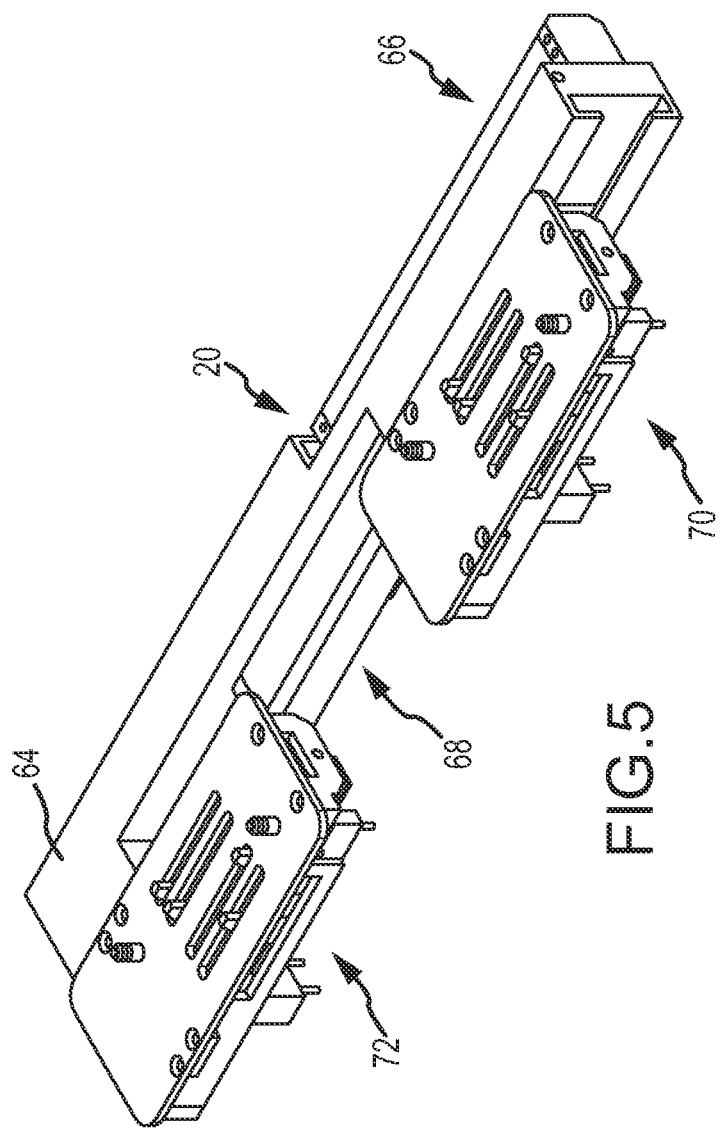
Figure 6:
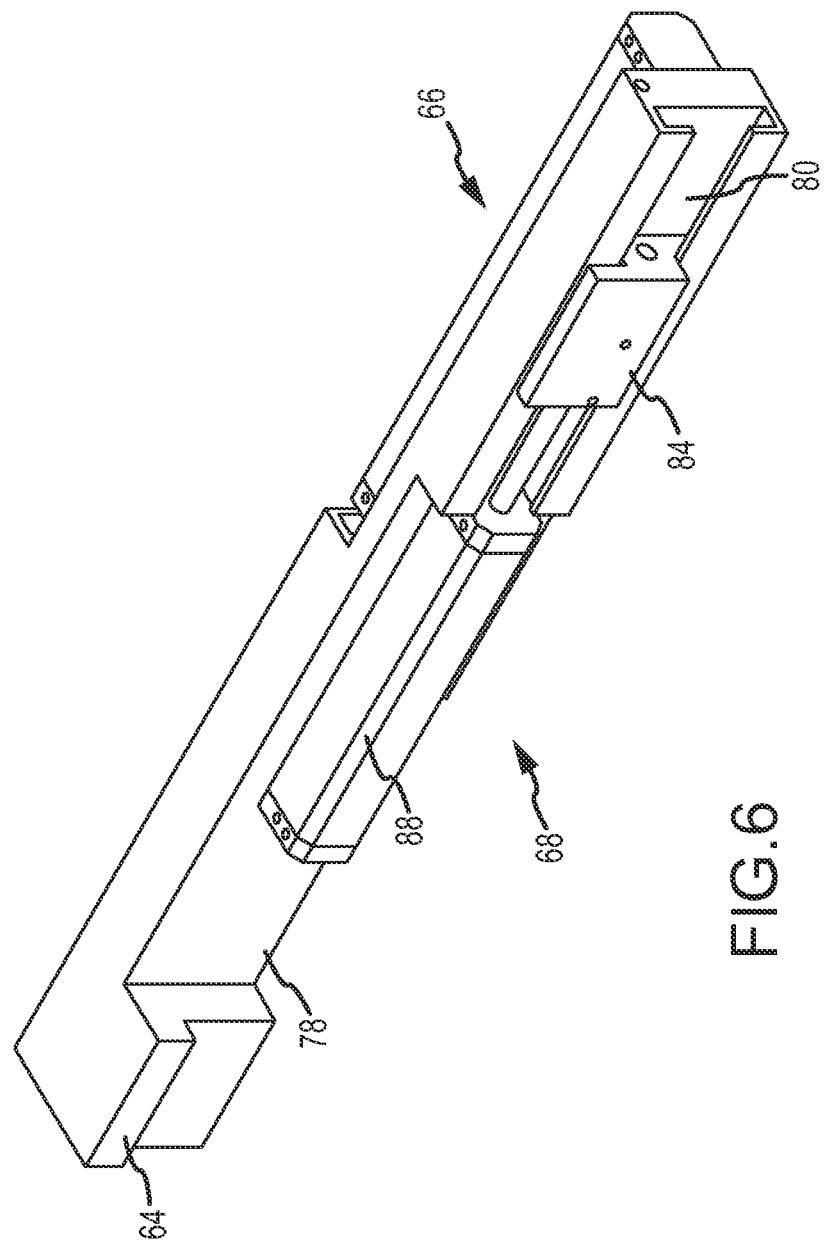
FIGS. 6-7 are perspective views of a portion of the assembly of FIGS. 4-5.
Figure 7:
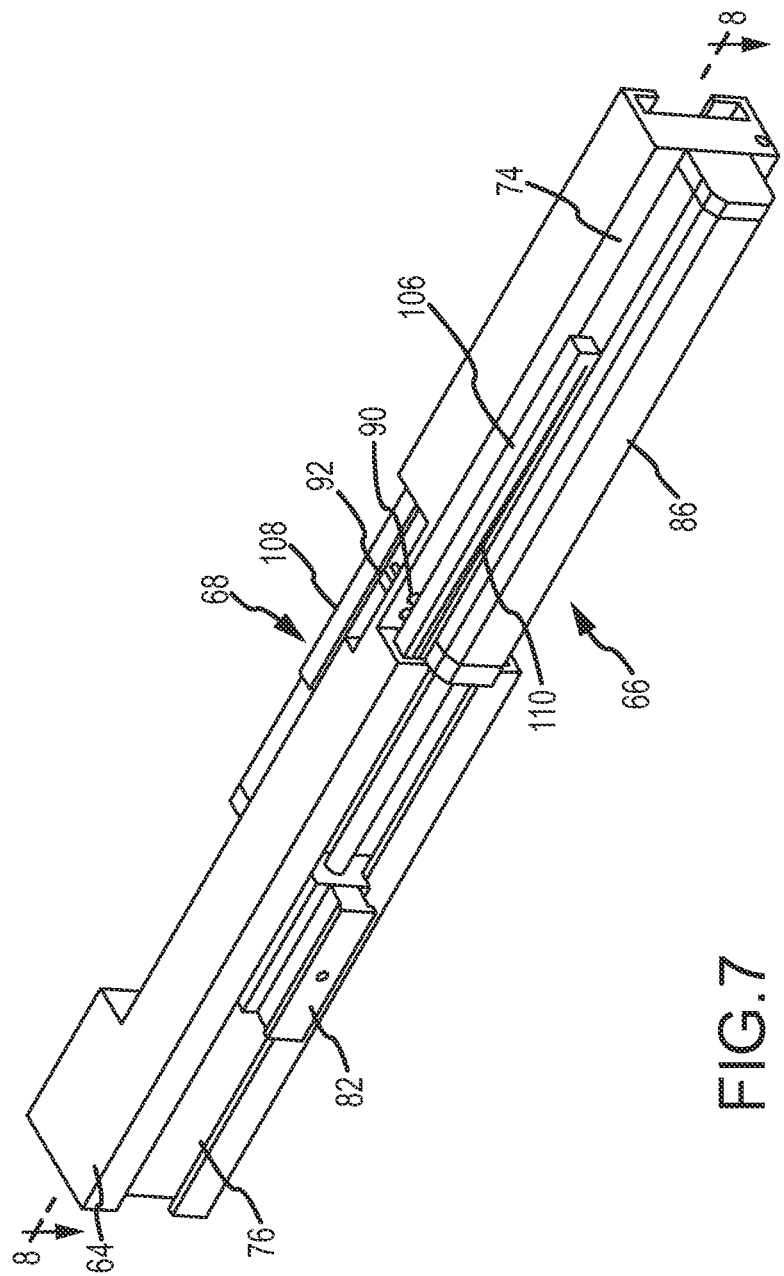
Figure 8:
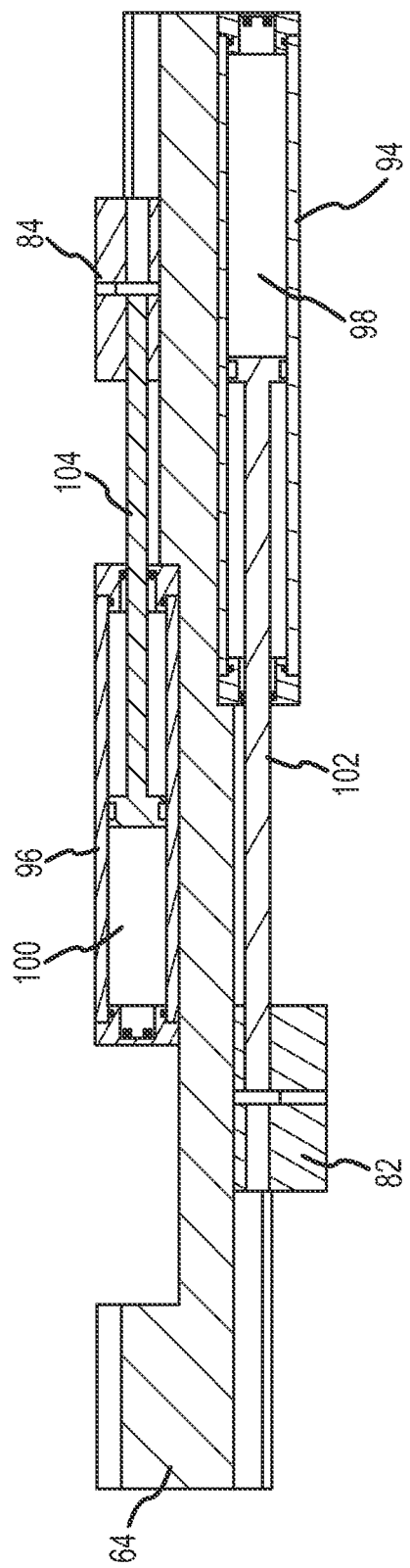
FIG. 8 is a cross-sectional view of a portion of the assembly of FIGS. 4-5, taken along lines 8-8 in FIG. 7.

Referring again to FIG. 1, manipulator assembly 20 is provided to manipulate one or more devices 12 in order to navigate the devices 12 within body 14. The components of manipulator assembly 20 may be disposed entirely within the operating environment 24 and are connected to fluid control system 18 in control environment 22 only through fluid conduits 26 and optic fibers 28 extending from sensors on assembly 20. Referring now to FIGS. 4-5, in one embodiment, manipulator assembly 20 is provided to manipulate both an introducer sheath 60 and a catheter 62. Assembly 20 may include a frame 64, a sheath translation drive assembly 66, a catheter translation drive assembly 68, a sheath deflection drive assembly 70 and a catheter deflection drive assembly 72. Translation drive assemblies 66, 68, and deflection drive assemblies 70, 72 are aligned so that sheath 60 and catheter 62 are coaxially aligned and catheter 62 can pass through sheath 60. In accordance with one aspect of the invention, all components of assembly 20—including components of assemblies 66, 68, 70, 72—may be non-magnetic and/or non-metallic thereby facilitating use of assembly 20 in environments that are subject to relatively high electromagnetic interference such as magnetic resonance imaging Referring now to FIGS. 6-8, frame 64 provides structural support to the other components of assembly 20. In the illustrated embodiment, frame 64 is generally rectangular in shape, but it should be understood that the configuration of frame 64 may vary depending on the device or devices 12 which assembly 20 controls. Frame 64 defines a recessed portion 74 and a channel 76 on one side configured to receive components of sheath translation drive assembly 66. Frame 64 further defines a recessed portion 78 and a channel 80 on an opposite side configured to received components of catheter translation drive assembly 68.

Sheath translation drive assembly 66 is provided to control translation of assembly 20 relative to body 14 and, as a result, sheath 60 and catheter 62 within body 14. Catheter translation drive assembly 68 is provided to control translation of catheter 62 within sheath 60 and within body 14. Assemblies 66, 68 may include slides 82, 84 fluid actuators 86, 88 and position sensors 90, 92 respectively.

Slide 82 is disposed within channel 76 of frame 64 and is configured to mount to a robotic arm (not shown) or similar structure used to orient assembly 20 relative to body 14. Slide 82 provides for movement of frame 64 relative to the robotic arm or similar structure. Slide 84 is disposed within channel 80 of frame 64 and is configured to support catheter drive deflection assembly 72 for movement of assembly 72 relative to frame 64 and sheath drive deflection assembly 70. It should be understood that the shape of slides 82, 84 may vary depending on the configuration and application of device or devices 12 supported by assembly 20. Slides 82, 84 may be supported on one or more linear bearings (not shown) within channels 76 80 on base 64 to facilitate movement of slides 82, 84 within channels 76, 80.

Fluid actuators 86, 88 are provided to control movement of slides 82, 84 within channels 76, 80 and, therefore, movement of assembly 20, sheath 60 and catheter 62. Actuators 86, 88 may include fluid housings 94, 96 defining fluid chambers 98, 100 (see FIG. 8) that may be coupled to appropriate supply and return fluid conduits 26S, 26R (see FIG. 2-3). Pistons 102, 104 are at least partially disposed within the fluid chambers 98, 100 and are coupled to slides 82, 84. Fluid provided to fluid chambers 98, 100 causes movement of pistons 102, 104 and slides 82, 84 to cause translation of assembly 20 and catheter deflection drive assembly 72 and movement of sheath 60 and catheter 62 relative to body 14. In accordance with one embodiment of the invention, pistons 102, 104 comprise double acting pistons and fluid housings 94, 96 include two ports at either longitudinal end of the housing with one port at each end coupled to a supply fluid conduit 26S and one port at each end coupled to a return fluid conduit 26R. The use of separate ports for conduits 26S, 26R facilitates purging of air from system 10 by eliminating any fluidic "dead space."Pressure sensors 40 (see FIGS. 2-3) may be used to measure pressure (and hence force) in return fluid conduit 26R.

Position sensors 90, 92 are configured to generate signals indicative of characteristics associated with movement of device 12 (and, in the illustrated embodiment, sheath 60 or catheter 62). In particular, sensors 90, 92 generate a signal indicative of the translation or movement of assembly 20 and of catheter drive deflection assembly 72 and, therefore, of sheath 60 and catheter 62. In accordance with one aspect of the invention, sensors 90, 92 include optic fibers 28 configured to transmit a light wave indicative of the measured characteristic. As used herein, the term "light wave" refers to an electromagnetic wave having a frequency and wavelength such that the wave would be classified as between and including the infrared and ultraviolet portions of the electromagnetic spectrum (e.g. a wavelength of between 10 and 100 nanometers). The use of optic fibers 28 and light based sensing as opposed to conventional electrical conductors enables use of system 10 in environments that are subject to relatively high levels of electromagnetic interference. Sensors 90, 92 may comprise fiber bragg grating sensors. Alternatively, sensors 90, 92 may comprise inferometers. In the case of fiber bragg grating sensors, the relatively narrow wavelength required for operation of the sensors 90, 92 enables the optic fibers 28 to be combined using a splitter (not shown) and directed to a common signal interrogator 50. Sensors 90, 92 are disposed proximate indicator blocks 106, 108 coupled to slides 82, 84, for movement therewith. Each indicator block 106, 108 may include a tapered slot 110 (see FIG. 7) that extends longitudinally along blocks 106, 108 in the direction of movement of slides 82, 84. A change in a position of blocks 106, 108 resulting from movement of slides 82, 84 causes a corresponding change in the light transmitted through or reflected from blocks 106, 108 and a corresponding change in output in sensors 90, 92 indicative of movement of sheath 60 and/or catheter 62.

Referring again to FIGS. 4-5, assemblies 70, 72 are provided to control deflection of sheath 60 and catheter 62, respectively, within body 14. Referring now to FIGS. 9-14, each of assemblies 70, 72 may include a mounting plate 112 and a plurality of fluid actuators 114 configured to independently control movement of corresponding steering wires (not shown) of sheath 60 or catheter 62. In accordance with another aspect of the present teachings, assemblies 70, 72 may further include a plurality of optic sensors 116, 118, 120 configured to generate signals indicative of characteristics associated with movement of sheath 60 and catheter 62.

Mounting plate 112 is provided for mounting a cartridge 122 or 124 (See FIG. 4) that houses sheath 60 or catheter 62. Plate 112 also provides a framework for connecting fluid actuators 114 to steering wires in sheath 60 or catheter 62. Cartridges 122, 124 may be disposable and will typically be affixed to plate 112 after the sheath 60 and catheter 62 have been manually inserted into the vascular system of the patient by the physician and roughly positioned near the region of interest within the body 14. The configuration of plate 112 may vary depending on the mounting arrangement required for cartridges 122, 124. Plate 112 may include a latch connector 126 configured for receipt in a corresponding socket in cartridge 122 or 124 and plate 112 and cartridge 122 or 124 may be snapped or locked together using various interfering structures such a spring detent. It should be understood that various mechanical locking features could be used. Plate 112 also includes a plurality of elongate apertures configured to align with corresponding apertures in cartridge 122 or 124 and through which a portion or a corresponding fluid actuator 114 extends for connection to actuators within cartridges 122, 124 coupled to steering wires for sheath 60 and catheter 62 thereby permitting independent tensioning of each steering wire.

Fluid actuators 114 are provided to control movement of steering wires in sheath 60 and catheter 62 in order to control deflection of the distal tip of sheath 60 and catheter 62. In the illustrated embodiment, four actuators 114 are provided to control a corresponding number of steering wires in sheath 60 or catheter 62 (e.g. in directions that result in a downward pull, upward pull, leftward pull and rightward pull of the tip of sheath 60 or catheter 62). Each actuator 114 may include a fluid housing 128, a deflection piston 130, a bias piston 132, and a steering wire connector 134.

Figure 12:
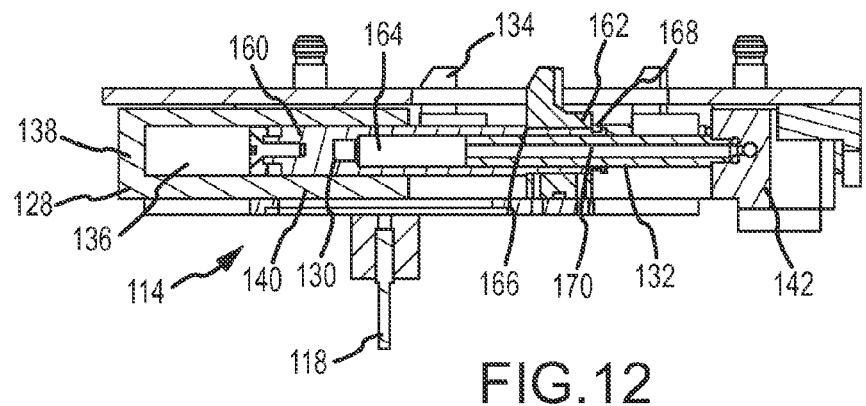
FIG. 12 is a cross-sectional view of the assembly of FIGS. 9-10 taken along lines 12-12 in FIG. 9.

Referring to FIG. 12, fluid housing 128 defines a fluid chamber 136 that stores a variable amount of fluid in response to fluid displacement through supply fluid conduit 26S by fluid control system 18 (See FIGS. 2-3). In the illustrated embodiment, a unitary structure defines four fluid housings 128 and corresponding fluid chambers 136. It should be understood, however, that physically separate fluid housings 128 and fluid chambers 136 could be formed. Fluid housing 128 is made from conventional materials based on the type of fluid used within system 10 (See FIG. 1). Fluid housing 128 may include several members 138, 140, 142 coupled together with adhesives or other conventional fastening mechanisms.

Figure 10:
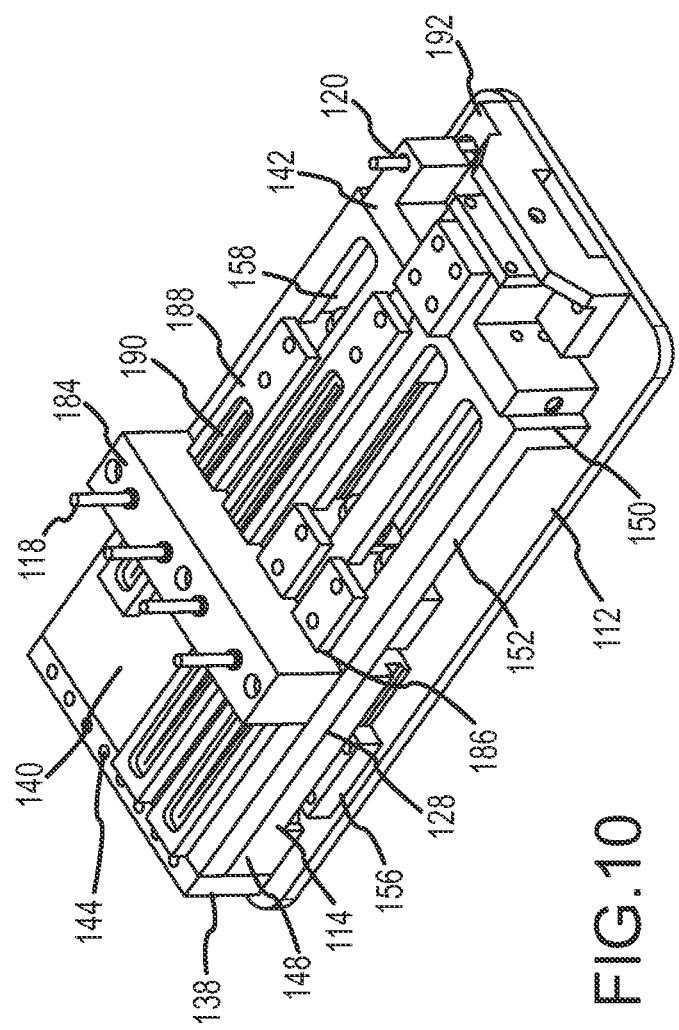

Member 138 is disposed at one end of assembly 72 or 74 and defines a fluid manifold through which fluid is routed to fluid chamber 136. Referring to FIG. 10, member 138 may include separate ports 144 for communication with supply and return fluid conduits 26S, 26R (See FIGS. 2-3). The use of separate ports 144 for conduits 26S, 26R facilitates purging of air from system 10 by eliminating any fluidic "dead space." Referring to FIG. 14, seals 146 prevent fluid loss at the connection of member 138 to member 140.

Figure 13:
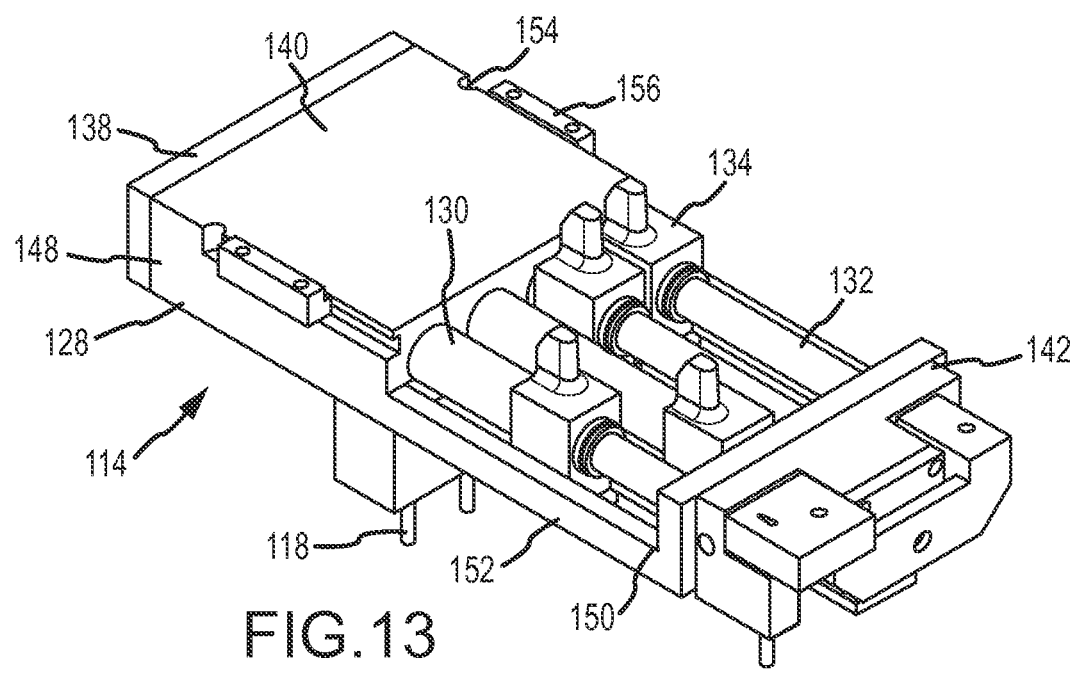
FIGS. 13-14 are perspective views of portions of the assembly of FIGS. 9-10.

Referring again to FIG. 12, member 140 defines fluid chamber 136. In the illustrated embodiment, member 140 also provides a frame for connection, support, and orientation of other components of assemblies 72, 74. Member 140 may be coupled directly to frame 64 (in the case of assembly 72) or indirectly via slider 84 (in the case of assembly 74) to secure assemblies 72, 74 on frame 64. Referring to FIG. 13, member 140 includes end portions 148, 150 and an intermediate portion 152. End portion 148 is adjacent member 138 and defines fluid chamber 136. An exterior surface of portion 148 defines channels 154 on each lateral side configured to receive slides 156 that are coupled to mounting plate 112 and permit movement of plate 112 relative to member 140. End portion 150 is configured to support bias piston 132 and connects to member 142 of housing 128. Intermediate portion 152 connects end portions 148, 150 and, with reference to FIG. 10, defines a plurality of elongate apertures 158 through which connectors 134 extend for a purpose discussed hereinbelow.

Member 142 of housing 128 is disposed at one end of assembly 72 or 74 and is connected to portion 150 of member 140. Member 142 defines a fluid manifold through which fluid is routed to a fluid chamber associated with bias piston 132 as discussed in greater detail hereinbelow.

Deflection piston 130 is provided to cause movement of a steering wire in sheath 60 or catheter 62 responsive to changes in fluid volumes within fluid chamber 136. Piston 130 is conventional in the art and may be made from conventional materials based on the type of fluid used within system 10. Referring to FIG. 12, a closed end 160 of piston 130 is disposed within fluid chamber 136. An opposite, open end 162 of piston 130 extends through connector 134. Open end 162 of piston 130 itself defines a fluid chamber 164 configured to receive one end of bias piston 132 for a purpose described hereinbelow. Connector 134 is secured against movement relative to piston 130 by a shoulder 166 formed in an exterior surface of piston 130 and engaging one side of connector 134 and a locking ring 168 disposed in a groove formed in end 162 of piston 130 and engaging an opposite side of connector 134. Movement of piston 130 within fluid chamber 136 responsive to displacement of fluid in fluid chamber 136 causes a corresponding movement of connector 134 and a steering wire of a medical device coupled thereto.

Bias piston 132 provides a means for biasing deflection piston 130 and those elements coupled to piston 130 such as connector 134 to a home position in the event of a loss of fluid pressure in chamber 120 resulting from, for example, power loss or a system failure. Bias piston 132 further applies a preload to seals in fluid chamber 136 and insures that system 10 always operate under a minimum pressure to eliminate any mechanical play by compressing air and minimizing compliance. One end of bias piston 132 is supported within portion 150 of member 140 of housing 128. An opposite end of piston 132 is disposed within fluid chamber 164 formed in deflection piston 130. Piston 132 includes a fluid lumen 170 extending therethrough through which fluid (e.g., pneumatic fluid) may be routed from member 142 of housing 128 to chamber 164 in piston 130.

Figure 14:
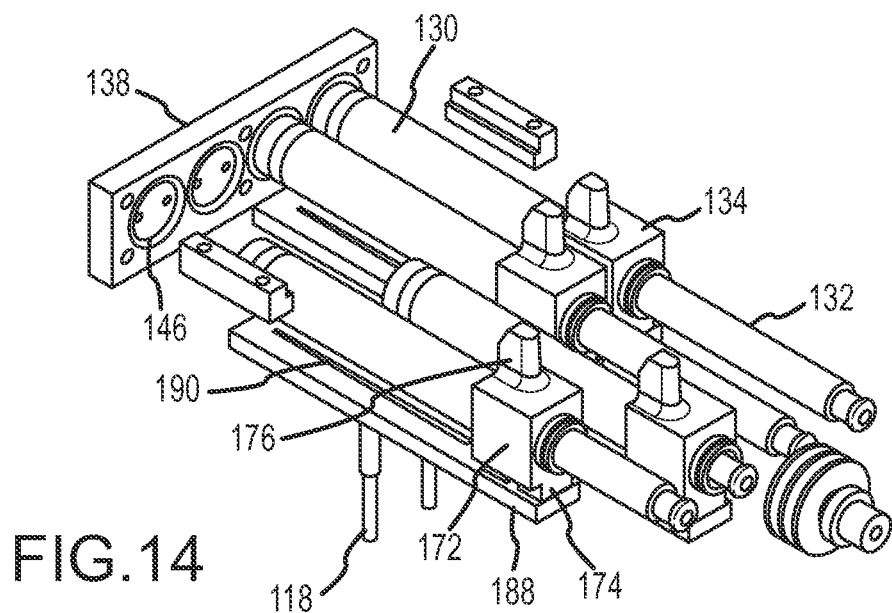

Connector 134 is configured for coupling to a steering wire in sheath 60 or catheter 62 such that movement of piston 130 within fluid chamber 136 causes corresponding movement of connector 134 and the steering wire. Connectors 134 also act as linear bearings to eliminate any lateral loads on pistons 130, 132. Referring to FIG. 14, in the illustrated embodiment, connector 134 includes a body 172 through which pistons 130, 132 extend and connect to one another. Body 172 includes a flange 174 extending from one side and through aperture 158 in portion 152 of member 140 of housing 128 for a purpose detailed hereinbelow. Body 172 includes a pin 176 extending from an opposite side of connector 134 configured for coupling to a steering wire in sheath 60 or catheter 62. It should be understood, however, that connector 134 could assume a wide variety of forms capable of coupling to a steering wire depending on the application.

Figure 9:
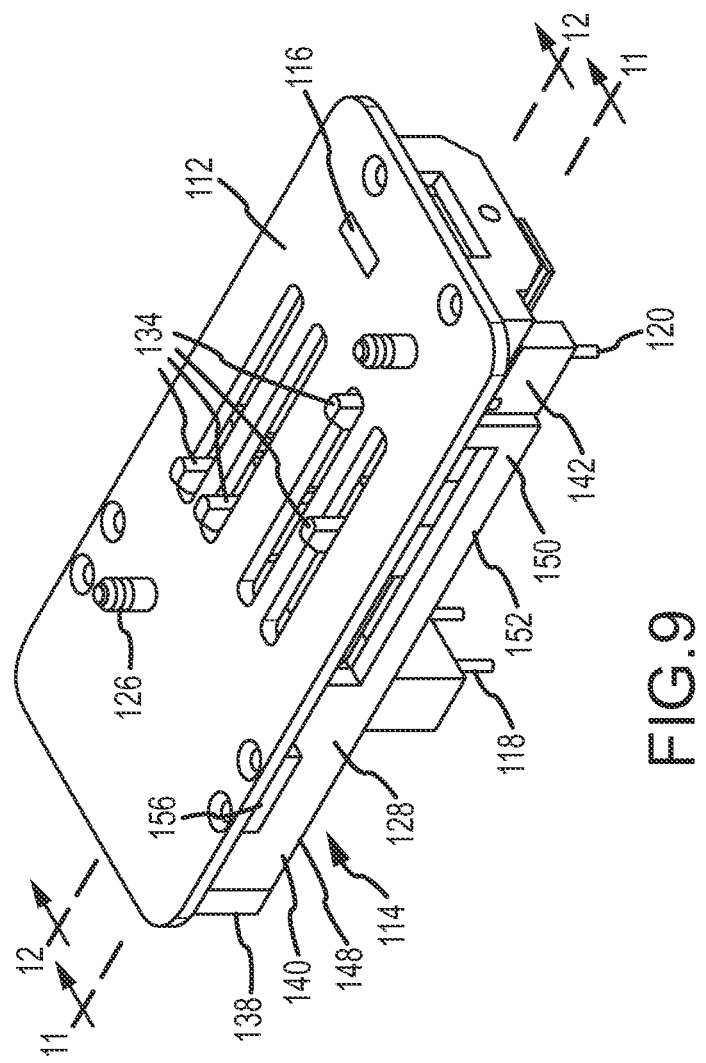
FIGS. 9-10 are perspective views of a catheter or sheath deflection drive assembly component of the manipulator assembly of FIGS. 4-5.
Figure 15:
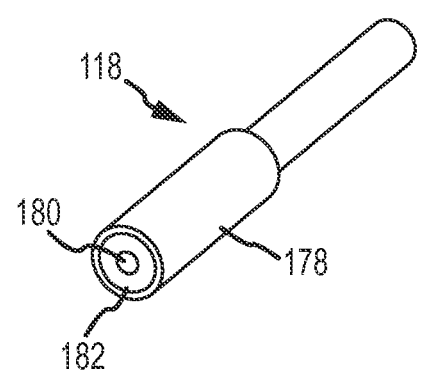
FIG. 15 is a perspective view of an optic sensor used in the assembly of FIGS. 9-10.

Referring to FIG. 9, for example, optic sensors 116, 118, 120 are configured to generate signals indicative of characteristics associated with movement of device 12 (and, in the illustrated embodiment, sheath 60 or catheter 62). In accordance with one aspect of the invention, sensors 116, 118, 120 include optic fibers 28 (FIG. 1) configured to transmit a light wave indicative of the measured characteristic. As used herein, the term "light wave" refers to an electromagnetic wave having a frequency and wavelength such that the wave would be classified as between and including the infrared and ultraviolet portions of the electromagnetic spectrum (e.g. a wavelength of between 10 and 100 nanometers). The use of optic fibers 28 and light based sensing as opposed to conventional electrical conductors enables use of system 10 in environments that are subject to relatively high levels of electromagnetic interference. Sensors 116, 118, 120 may comprise fiber bragg grating sensors. Alternatively, sensors 116, 118, 120 may comprise inferometers. In the case of fiber bragg grating sensors, the relatively narrow wavelength required for operation of the sensors 116, 118, 120 enables the optic fibers 28 to be combined using a splitter (not shown) and directed to a common signal interrogator 50. Referring to FIG. 15, in accordance with one embodiment of the invention, sensors 116, 118, 120 may comprise two or more optic fibers 28 (FIG. 1) terminating in a head 178 and forming concentric members 180, 182 wherein one of members 180, 182 is an emitter and the other is a detector.

Sensors 116, 118, 120 may be provided to generate a variety of data including information for use by the physician and feedback information for ECU 52. In accordance with one embodiment according to the present teachings, sensors 116, 118, 120 are provided to generate one or more signals indicative of characteristics associated with movement of device 12. In the illustrated embodiment, for example, sensor 116 generates a signal indicative of a state of mechanical coupling of device 12 to manipulator assembly 20 and, particularly, to connector 134 of assemblies 70, 72. Sensor 116 may, for example, detect the connection of one of the steering wires in sheath 60 or catheter 62 to connectors 134. Alternatively, sensor 116 may detect the attachment of cartridge 122 or 124 to assemblies 70, 72.

Sensors 118 generate signals indicative of a position of a corresponding steering wire along a steering wire axis. Referring to FIG. 10, sensors 118 may be mounted in a housing 184 coupled to the underside of portion 148 of member 140 of housing 128. Housing 184 defines a plurality of passages 186 configured to receive corresponding indicator blocks 188. Each block 188 is coupled to flange 174 (see FIG. 14) of a corresponding connector 134. Each indicator block 188 may include a tapered slot 190 that extends longitudinally along block 188 in the direction of movement of connector 134. A change in a position of block 188 resulting from movement of connector 134 causes a corresponding change in the light transmitted or reflected from block 188 and a corresponding change in output in sensor 118 indicative of movement of sheath 60 and/or catheter 62.

Figure 11:
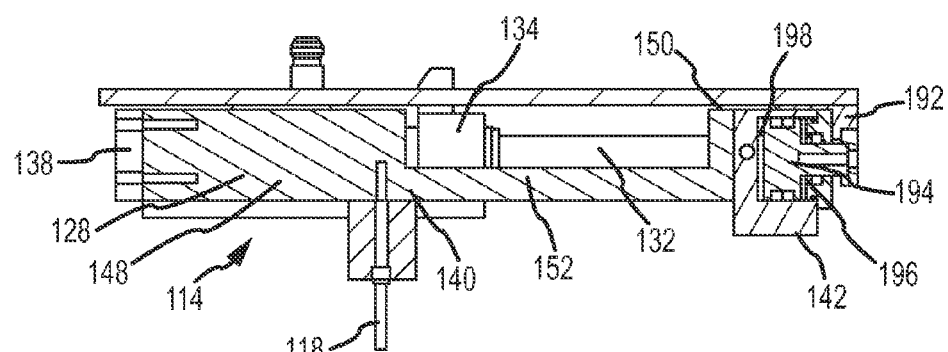
FIG. 11 is a cross-sectional view of the assembly of FIGS. 9-10 taken along lines 11-11 in FIG. 9.

Sensor 120 generates a signal indicative of a translation force applied to sheath 60 or catheter 62. Referring to FIG. 10, sensor 120 may be supported within member 142 of housing 128 and is positioned relative to an indicator (e.g., a tapered slot similar to those found in blocks 188) whose position changes responsive to a translation force applied to sheath 60 or catheter 62. In the illustrated embodiment, the indicator is formed in a frame member 192 coupled to mounting plate 112. Referring to FIG. 11, member 192 supports a sealed double acting piston 194 extending through a cylinder head 196 and into a fluid chamber 198 formed in member 142 of housing 128. The piston 194 has a predetermined home position somewhere between the end points of its stroke. Movement of piston 194 in either direction within chamber 198 and away from the home position results in a corresponding movement of frame member 192 and a change in the output of sensor 120 thereby providing an indication of the translation force applied along a steering wire axis. Piston 194 could be moved in a dithering action to minimize or eliminate frictional effects of seals and inertia affects of the fluid drives.

Figure 16:
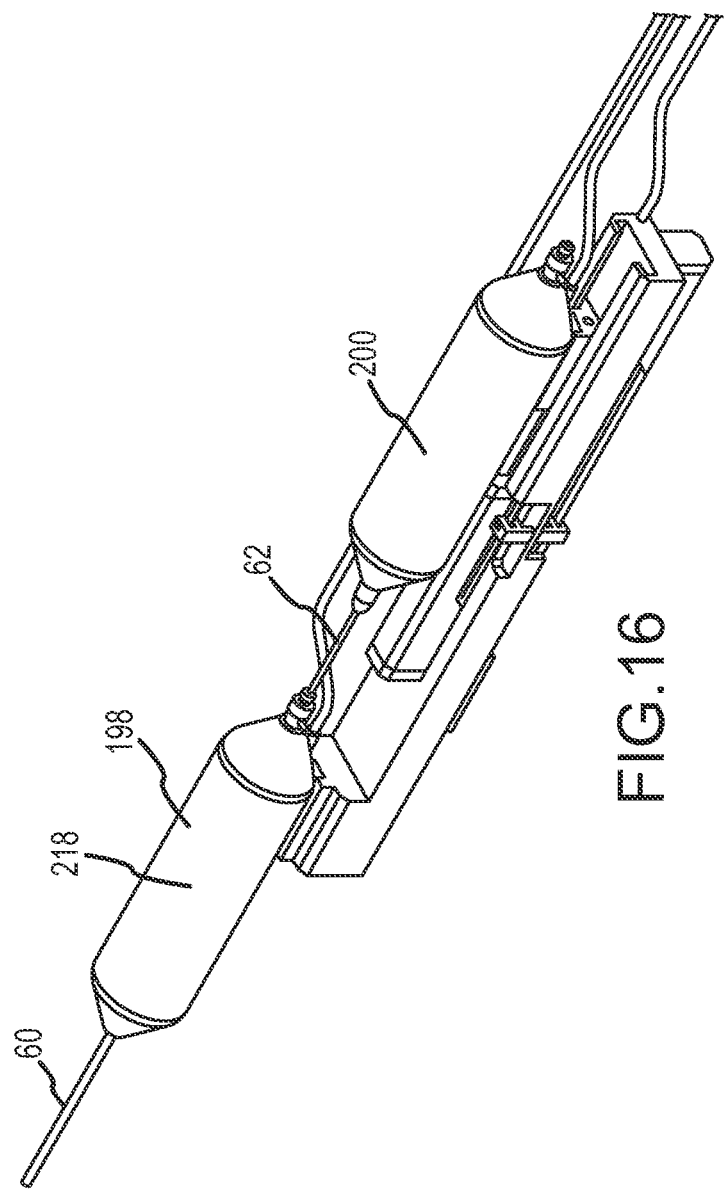
FIG. 16 is a perspective view of another embodiment of a manipulator assembly for use in the remote guidance system of FIG. 1.

Referring now to FIG. 16, a manipulator assembly 196 in accordance with another embodiment of the present teachings for use in system 10 is illustrated. Assembly 196 may be substantially similar to system 20 (FIG. 4) and descriptions for similar components may be found hereinabove. Assembly 196 differs from assembly 20 in that assembly 196 includes modified sheath and catheter deflection drive assemblies 198, 200.

Figure 17:
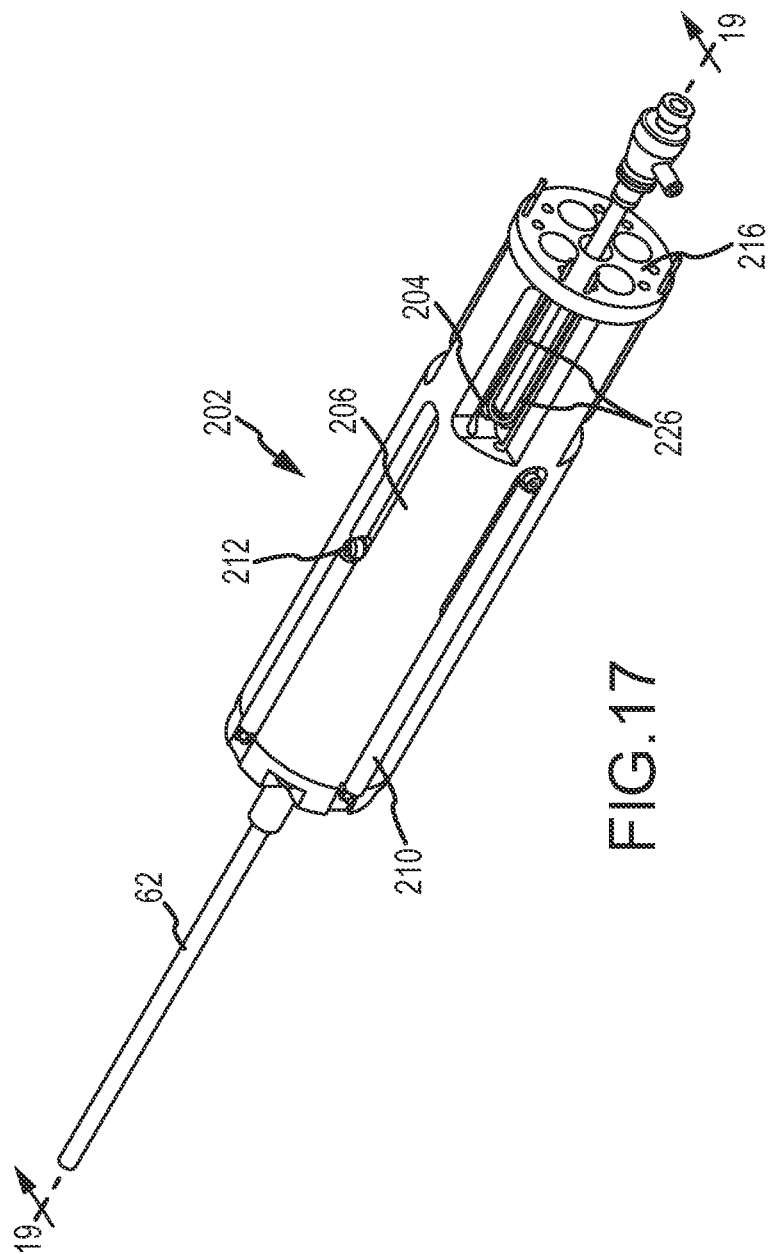
FIG. 17 is a perspective view of a portion of the assembly of FIG. 16.
Figure 18:
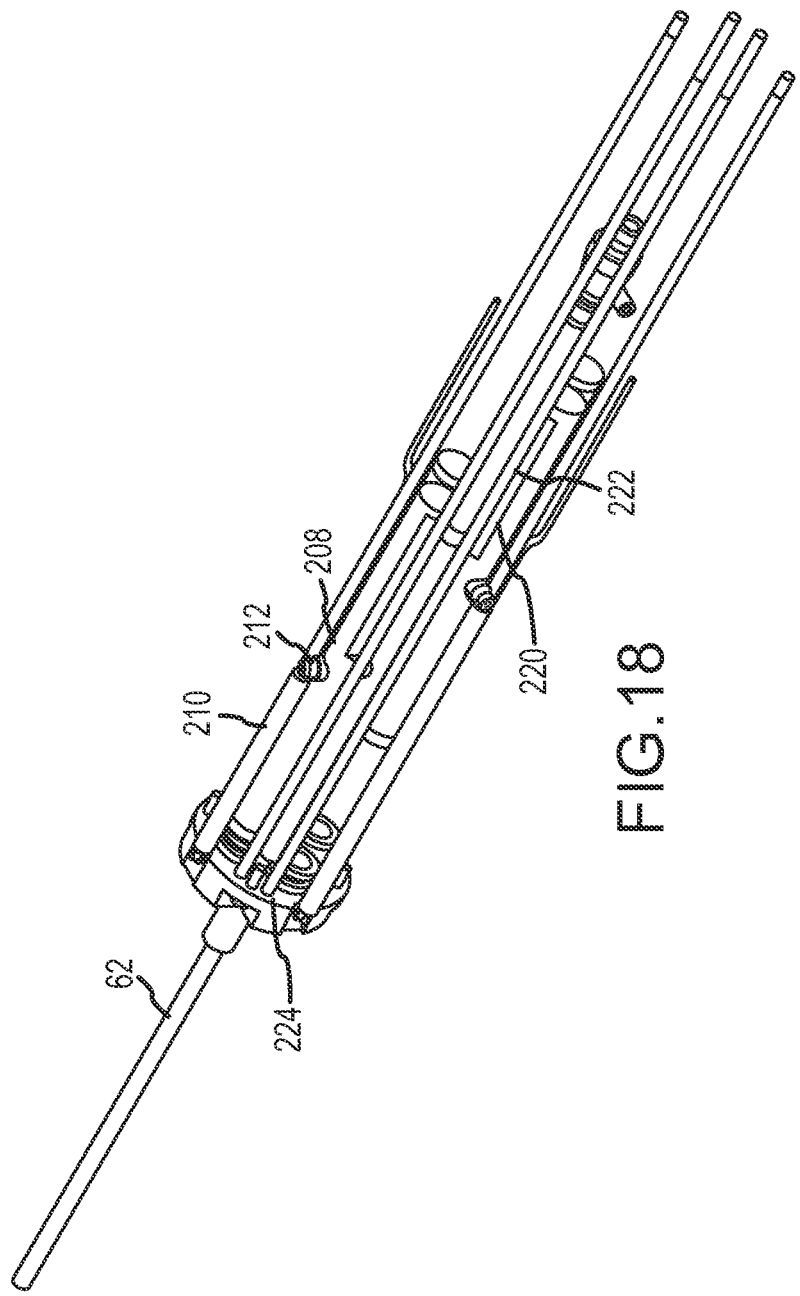
FIG. 18 is a perspective view of a portion of the assembly of FIG. 16.
Figure 19:
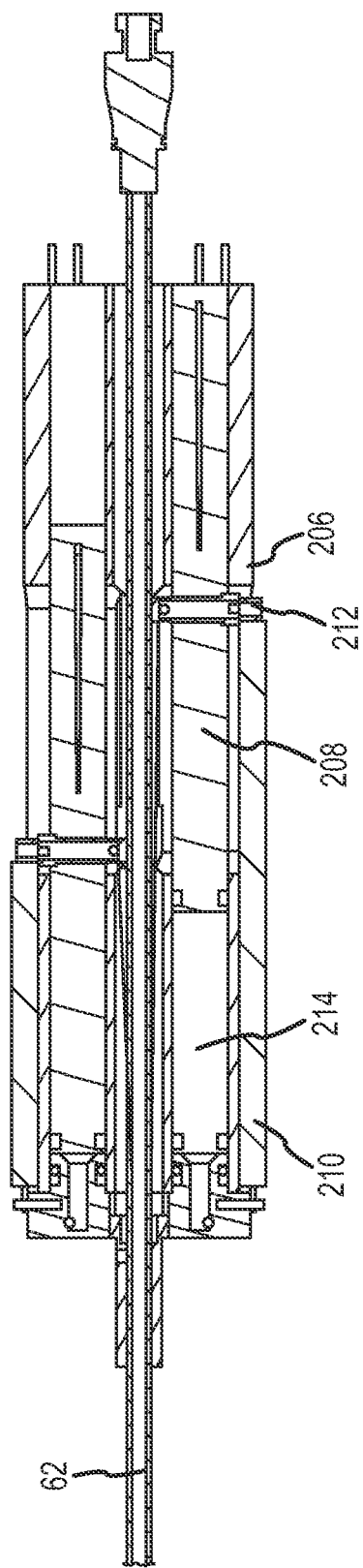
FIG. 19 is a cross-sectional view of a portion of the assembly of FIG. 16, taken along lines 19-19 in FIG. 17.

Assemblies 198, 200 are again provided to control deflection of sheath 60 and catheter 62, respectively, within body 14. Assemblies 198, 200, however, integrate the functionality of drive assemblies 72, 74 with that of cartridges 122, 124. Referring now to FIGS. 17-19, each of assemblies 198, 200 may include a plurality of fluid actuators 202 configured to independently control movement of corresponding steering wires (not shown) of sheath 60 or catheter 62. In accordance with another aspect of the present teachings, assemblies 198, 200 may further include a plurality of optic sensors 204 configured to generate signals indicative of characteristics associated with movement of sheath 60 and catheter 62.

Fluid actuators 202 are provided to control movement of steering wires in sheath 60 and catheter 62 in order to control deflection of the distal tip of sheath 60 and catheter 62. In the illustrated embodiment, four actuators 202 are provided to control a corresponding number of steering wires in sheath 60 or catheter 62 (e.g. in directions that result in a downward pull, upward pull, leftward pull and rightward pull of the tip of sheath 60 or catheter 62). Each actuator 202 may include a fluid housing 206, a deflection piston 208, a bias piston 210, and a steering wire connector 212.

Referring to FIG. 19, fluid housing 206 defines a fluid chamber 214 that stores a variable amount of fluid in response to fluid displacement through supply fluid conduit 26S by fluid control system 18 (FIG. 1). In the illustrated embodiment, a unitary structure again defines four fluid housings joined fluid housings 206 and corresponding fluid chambers 214. It should be understood, however, that physically separate fluid housings 206 and fluid chambers 214 could be formed. Fluid chambers 214 are disposed circumferentially about a central axis in the illustrated embodiment and may be spaced at equal circumferential distances. Fluid housing 206 is made from conventional materials based on the type of fluid used within system 10 (FIG. 1). Fluid housing 206 may also provide a structural frame for connection, support, and orientation of other components of assemblies 198, 200 and define a manifold for routing fluid conduits 26S, 26R and optic fibers 28 (FIG. 1). Referring to FIG. 17, housing 206 may again define separate ports 216 for communication with supply and return fluid conduits 26S, 26R. The use of separate ports for conduits 26S, 26R facilitates purging of air from system 10 by eliminating any fluidic "dead space." Referring to FIG. 16, housing 206 may be disposed within an outer assembly housing 218 that may be coupled directly to frame 64 (in the case of assembly 198) or indirectly via slider 84 (in the case of assembly 200) to secure assemblies 198, 200 on frame 64.

Referring again to FIGS. 15-17, deflection piston 208 is provided to cause movement of a steering wire in sheath 60 or catheter 62 responsive to changes in fluid volumes within fluid chamber 214. Piston 208 is conventional in the art and may be made from conventional materials based on the type of fluid used within system 10. Referring to FIG. 18, connector 212 extends radially outwardly from piston 208 and is configured for connection to a steering wire for sheath 60 or catheter 62. A radially outer surface of piston 208 also defines a flat 220 proximate one end. Flat 220 includes a position indicator such as tapered slot 222 for a purpose described hereinbelow.

Bias piston 210 provides a means for biasing deflection piston 208 and those elements coupled to piston 208 such as connector 212 to a home position in the event of a loss of fluid pressure in chamber 214 resulting from, for example, power loss or a system failure. Bias piston 210 further applies a preload to seals in fluid chamber 214 and insures that system 10 always operate under a minimum pressure to eliminate any mechanical play by compressing air and minimizing compliance. Referring to FIG. 18 one end of each bias piston 210 is disposed against a mount on cylinder head 224 disposed at an end of housing 208. The opposite end of each bias piston 210 is disposed against a corresponding connector 212.

Connector 212 is configured for coupling to a steering wire in sheath 60 or catheter 62 such that movement of piston 208 within fluid chamber 214 causes corresponding movement of connector 212 and the steering wire. Connectors 212 also acts linear bearings to eliminate any lateral loads on pistons 208, 210. In the illustrated embodiment, connector 212 is generally round and extends radially outwardly from piston 208. It should be understood, however, that connector 212 could assume a wide variety of forms capable of coupling to a steering wire depending on the application.

Optic sensors 204 are configured to generate signals indicative of characteristics associated with movement of device 12 (and, in the illustrated embodiment, sheath 60 or catheter 62). In accordance with one aspect of the invention, sensors 204 include optic fibers 28 configured to transmit a light wave indicative of the measured characteristic. As used herein, the term "light wave" refers to an electromagnetic wave having a frequency and wavelength such that the wave would be classified as between and including the infrared and ultraviolet portions of the electromagnetic spectrum (e.g. a wavelength of between 10 and 100 nanometers). The use of optic fibers 28 and light based sensing as opposed to conventional electrical conductors enables use of system 10 in environments that are subject to relatively high levels of electromagnetic interference. Sensors 204 may comprise fiber bragg grating sensors. Alternatively, sensors 204 may comprise inferometers. In the case of fiber bragg grating sensors, the relatively narrow wavelength required for operation of the sensors 204 enables the optic fibers 28 to be combined using a splitter (not shown) and directed to a common signal interrogator 50.

Sensors 204 may be provided to generate a variety of data including information for use by the physician and feedback information for ECU 52. In accordance with one embodiment according to the present teachings, sensors 204 are provided to generate one or more signals indicative of characteristics associated with movement of device 12. In the illustrated embodiment, sensors 204 generate signals indicative of a position of a corresponding steering wire along a steering wire axis. Referring to FIG. 17, sensors 204 may include a collimated fiber optic emitter/detector pair 226 disposed proximate slot 222 on a corresponding piston 208. A change in a position of piston 208, and therefore connector 212 causes a corresponding change in the light transmitted or reflected and a corresponding change in output in sensor 204 indicative of movement of sheath 60 and/or catheter 62.

A remote guidance system for a medical device in accordance with the present teachings is advantageous relative to conventional remote guidance systems because the use of fluid based controls and/or optic sensors enable use of the remote guidance system in environments that are subject to relatively high electromagnetic interference such as magnetic resonance imaging. As a result, the benefits of remote guidance systems, including precise control of the medical device within the body, can be obtained in such environments. Further, the components forming the remote guidance system in the operating environment 24 can be manufactured entirely from non-magnetic materials, such as polymeric materials and other non-metallic materials because little or no electrical signals or conduction are required which may result in less cost and simplified manufacture.

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A remote guidance system for navigating a medical device within a body, said remote guidance system comprising:
   a fluid control system configured to control delivery of fluid to a first fluid conduit;
   a first fluid actuator, comprising:
      a first fluid housing defining a fluid chamber and configured to receive fluid from said first fluid conduit;
      a first piston disposed within said fluid chamber and movable within said fluid chamber responsive to a change in fluid displacement within said fluid chamber; and, a connector disposed outside of the medical device and coupled to said first piston and configured for coupling to a first steering wire in the medical device at a location outside of the body wherein the first fluid actuator is configured such that movement of said first piston causes corresponding movement of said connector and said first steering wire and a corresponding first movement of the medical device within the body.

2. The remote guidance system of claim 1 further comprising:

a second fluid actuator, comprising:

a second fluid housing defining a fluid chamber and configured to received fluid from a second fluid conduit, said fluid control system configured to control delivery of fluid to said second fluid conduit; and, a second piston disposed within said fluid chamber of said second fluid housing and movable within said fluid chamber of said second fluid housing responsive to a change in fluid displacement within said fluid chamber of said second fluid housing;

wherein the second fluid actuator is configured such that movement of said second piston causes a corresponding second movement of the medical device within the body.

3. The remote guidance system of claim 1 wherein said first movement of the medical device comprises translation of the medical device within the body.

4. The remote guidance system of claim 1 wherein said first movement of the medical device comprises deflection of a distal tip of the medical device within the body.

5. The remote guidance system of claim 1 wherein said fluid control system includes:

an electric motor;

a second fluid housing coupled to said first fluid conduit and defining a fluid chamber;

a second piston coupled to said motor and disposed within said fluid chamber of said second fluid housing and movable within said fluid chamber of said second fluid housing to control an amount of fluid in said first fluid conduit and said fluid chamber of said first fluid housing; and an electronic control unit configured to control said electric motor.

6. The remote guidance system of claim 5 further comprising:

a linear actuator coupled to said second piston and configured to move said second piston within said fluid chamber of said second cylinder responsive to an output force of said motor.

7. The remote guidance system of claim 1 wherein said fluid control system includes:

a motor;

a fluid pump configured to be driven by said motor and provide fluid to said first fluid conduit; and, a valve configured to control fluid flow in said first conduit; and, an electronic control unit configured to control said valve.

8. The remote guidance system of claim 1 further comprising:

a pressure sensor configured to sense fluid pressure in a second fluid conduit coupled to said fluid chamber and through which fluid exits said fluid chamber.

9. The remote guidance system of claim 1 wherein said first fluid actuator further includes means for biasing said first piston to a home position.

10. The remote guidance system of claim 1 further comprising a first sensor configured to generate a signal indicative of a first characteristic associated with movement of the medical device, said first sensor including a first optic fiber configured to transmit a detected light wave indicative of the first characteristic.

11. The remote guidance system of claim 10 further comprising a second sensor configured to generate a signal indicative of a second characteristic associated with movement of the medical device, said second sensor including a second optic fiber configured to transmit a detected light wave indicative of the second characteristic.

12. The remote guidance system of claim 10 wherein the first characteristic comprises a position of the first steering wire of the medical device along an axis.

13. The remote guidance system of claim 10 wherein the first characteristic comprises a force applied to the first steering wire of the medical device along an axis.

14. The remote guidance system of claim 10 wherein the first characteristic comprises a state of mechanical coupling of the medical device to said first piston.

15. The remote guidance system of claim 10 wherein said first sensor comprises a fiber bragg grating sensor.

16. The remote guidance system of claim 10 wherein said first sensor comprises an inferometer.

17. The remote guidance system of claim 10 wherein said first sensor is configured to generate an emitted light wave from one of said first optic fiber and a second optic fiber, wherein said first sensor is configured to transmit the detected light wave generated in response to a reflection of said emitted light wave.

18. The remote system of claim 10 wherein said first sensor generates an emitted light wave from one of said first optic fiber and a second optic fiber, wherein said first sensor is configured to transmit the detected light wave generated in response to an attenuation of said emitted light wave.

19. The remote guidance system of claim 1 wherein the medical device comprises a catheter.

20. The remote guidance system of claim 1 wherein the medical device comprises an introducer sheath.

21. The remote guidance system of claim 1 wherein said first fluid actuator is made from only non-magnetic materials.

22. A remote guidance system for guiding a medical device within a body, said remote guidance system comprising:

a connector disposed outside of the medical device and configured for coupling to a first steering wire of the medical device at a location outside of the body, and wherein the connector is further configured such that movement of said connector causes a corresponding movement of the first steering wire and of the medical device within the body;

means for controlling movement of said connector; and, a first sensor generating a signal indicative of a first characteristic associated with movement of said device, said first sensor including a first optic fiber configured to transmit a detected light wave indicative of the first characteristic.

23. The remote guidance system of claim 22 wherein said first sensor is configured to generate an emitted light wave from one of said first optic fiber and a second optic fiber, wherein said first sensor is further configured to transmit the detected light wave generated in response to a reflection of said emitted light wave.

24. The remote guidance system of claim 22 wherein said first sensor is configured to generate an emitted light wave from one of said first optic fiber and a second optic fiber, wherein said first sensor is configured to transmit the detected light wave generated in response to an attenuation of said emitted light wave.

25. The remote guidance system of claim 22 wherein said controlling means is made from only non-magnetic materials.

26. A remote guidance system for steering a medical device within a body, said remote guidance system comprising:
- a fluid control system configured to control delivery of fluid to a fluid conduit;
- a manipulator assembly operably coupled to said fluid conduit, said manipulator assembly comprising:
- a first connector disposed outside of the medical device and configured to couple with a steering wire of the medical device at a location outside of the body; and
- a second connector configured to releasably hold the medical device to a fluid actuator at a location outside the body;
- wherein the manipulator assembly is configured such that when fluid is delivered to the manipulator assembly from the fluid control system, the first connector moves relative to the second connector and such movement causes corresponding movement of said steering wire and causes the medical device to move within the body; and
- an electronic control unit configured to control said fluid control system.

* * * * *